United States Patent [19]

Pollard

[11] Patent Number: 4,661,453
[45] Date of Patent: Apr. 28, 1987

[54] PRODUCTION OF TISSUE PLASMINOGEN ACTIVATOR FACTOR

[75] Inventor: Morris Pollard, South Bend, Ind.

[73] Assignee: American Biogenetic Sciences, Inc., Copiague, N.Y.

[21] Appl. No.: 622,182

[22] Filed: Jun. 19, 1984

[51] Int. Cl.⁴ .................. C12N 9/48; C12N 9/72; C12N 9/50
[52] U.S. Cl. .................. 435/212; 435/215; 435/219
[58] Field of Search .................. 435/68, 70, 212, 215, 435/219, 226, 240, 948

[56] References Cited

U.S. PATENT DOCUMENTS

| | | | |
|---|---|---|---|
| 3,904,480 | 9/1975 | Hull et al. | 435/240 |
| 3,930,945 | 1/1976 | Lewis | 435/215 |
| 4,066,506 | 1/1978 | Johnson et al. | 435/215 |
| 4,317,882 | 3/1982 | Horiguchi et al. | 435/215 |
| 4,328,314 | 5/1982 | Horiguchi et al. | 435/212 |

FOREIGN PATENT DOCUMENTS

83/03101 9/1983 World Int. Prop. O. .......... 435/226

OTHER PUBLICATIONS

Strickland et al, "Purification and Properties of a Plasminogen Activator from Cultured Rat Prostate Adenocarcinoma", Biochemistry 22 p. 4444–9 (1983).
Rennie et al, "Plasminogen Activator in Prostatic Tumors of Nb Rats".
Biochinica et Biophysica Acta 632 p. 437–43 (1980).
Lechner et al, "Nutrition of Prostate Cells," Prog. Clin. Biol. Res., 37, p. 217–32 (1980) Chem. Abst. 93: 43358k.

Primary Examiner—Charles F. Warren
Assistant Examiner—John Edward Tarcza
Attorney, Agent, or Firm—Pennie & Edmonds

[57] ABSTRACT

A process for the production of a tissue plasminogen activator obtained from cultured rat prostate adenocarcinoma cells. The techniques described lead to enhanced production of the tissue plasminogen activator for markedly prolonged periods of time. The tissue plasminogen activator so produced may be used for the treatment of thrombosis.

17 Claims, No Drawings

PRODUCTION OF TISSUE PLASMINOGEN ACTIVATOR FACTOR

TABLE OF CONTENTS

1. Field of the Invention
2. Background of the Invention
3. Summary of the Invention
4. Description of the Invention
   4.1. Development of a TPA Producing Cell Line
   4.2. Production of TPA by Cells in Confluent Monolayers and Collection of Culture Medium
   4.3. Purification of TPA from the Culture Medium
5. Example: PA III Cells
   5.1. Conditions for the Optimal Production of TPA by Cultured PA III Cells
      5.1.2. Origin and Establishment of the PA III Cell Line
   5.2. Characterization of TPA Produced by PA III Cells in Culture
      5.2.1. Measurement of Plasminogen Activator Thrombolytic Activity in the PA III Culture Medium
      5.2.2. Binding to Fibrin and Fibrinolytic Activity
      5.2.3. Molecular Weight of the TPA Produced
      5.2.4. Neutralization of TPA Activity by Specific Antisera
   5.3. Deposit of the PA III Cell Line

1. FIELD OF THE INVENTION

This invention relates to a process for the production of a tissue plasminogen activator obtained from cultured rat prostate adenocarcinoma cells. This process utilizes novel tissue culture techniques that lead to enhanced production of the plasminogen activator for markedly prolonged periods of time. The tissue plasminogen activator so produced can be isolated from the cell culture medium. The tissue plasminogen activator prepared according to the method of the present invention may be used for the treatment of thrombosis without the complications of systemic plasminogenolysis and hemorrhaging that may accompany the use of currently available urokinase or streptokinase plasminogen activators.

2. BACKGROUND OF THE INVENTION

The occlusion of blood vessels and capillaries by blood clots is the most frequent cause of mortality in the developed world. The process of blood clotting, called thrombosis, involves a complex system of interacting enzyme factors, each of which is converted by other enzymes from an inactive to an active form. As a result of the overall activity of this system, protein fibers called fibrin become enmeshed in a mass which curtails blood flow at the point of the thrombosis. Where such thrombosis occurs at the site of a cut, the effect is the protective reduction of blood loss through bleeding. But where such thrombosis occurs in a uncontrolled manner in major arteries supplying the lungs, brain or other vital organs, the result may be paralysis, loss of neural function, or death, unless the fibrin clot can be removed expeditiously.

The removal of fibrin clots may sometimes be effected by surgical means, but this is not always practicable. Fortunately, however, there is a physiological system that can reverse the thrombosis process by dissolving the fibrin clots. (For a review of this system, see Gronow and Bliem, 1983, Trends in Biotech. 1: 26–29)

At the heart of this system is plasmin, an enzyme that can degrade the large, insoluble fibrin mass to small, soluble components. Plasmin, however, is normally present in the body in an inactive precursor form, called plasminogen. Plasminogen may be converted to plasmin through a single enzymatic cleavage of its polypeptide structure, by a member of a family of specific hydrolase enzymes called plasminogen activators (PAs). These PAs are believed to be serine hydrolases, because they are inhibited by the relatively serine-specific enzyme inhibitor diisopropyl fluorophosphate (DFP).

On the basis of neutralization by specific antisera and affinity for fibrin, PAs may be divided into two broad categories. The first group is related to urokinase, which can be isolated from human urine and is produced by the cells which line the kidney tubules. These "urokinase-like" PAs (UPAs) may be readily identified by the fact that their activity is neutralized by anti-urokinase antiserum. Furthermore, UPAs, another example of which is streptokinase of bacterial origin, can be distinguished from the other broad category of PAs by the fact that they do not bind to fibrin. This observation is of practical importance in the therapeutic removal of fibrin clots; since urokinase and streptokinase have no affinity for fibrin, much larger quantities of these UPAs must be used to dissolve fibrin clots. Furthermore, the large excess of UPAs that is required may produce undesired systemic plasminogenolysis, with concomitant internal hemorrhaging.

The second broad category of PAs is the group of "tissue-like" PAs (TPAs). This type of PA, which is produced by human lung and many other tissues and by numerous mammalian tumor cells, is not neutralized by anti-urokinase antiserum. Antiserum prepared against one TPA will neutralize other TPAs as well, but not the UPAs. The TPA class of plasminogen activators also binds to fibrin clots. As a result, the conversion of plasminogen to plasmin by TPAs tends to occur only at the site where it is needed, rather then systemically. Therefore, TPAs may be used in much lower therapeutic concentrations, a fact which would make thrombosis therapy with TPAs much less costly and far safer.

Plasminogen activators may be isolated from numerous sources. They may be found, for example, in blood, tears, saliva, urine, semen and in cerebrospinal or other body fluids (Gronow and Bliem, 1983, Trends in Biotech. 1: 26–29) They may also be found in many tissues and cells. Wilson et al. (Cancer Research, 1980, 40: 933–938) have found PAs in human embryo fibroblasts, bladder, lung, brain, thyroid, kidney, skin, foreskin fibroblasts and epithelium, and fallopian tube epithelium.

It has long been known that many tumor cells also produce PAs (Rifkin et al., 1974, J. Exp. Med. 139: 1317–1328). Many investigators believe that the ability of tumor cells to produce PAs contributes to their tendency to metastasize and thus, at least in part, facilitates the spread of neoplastic disease. In any event, the fact that tumor cells are easily cultured and that they often produce PAs has made possible the production of substantial quantities of PAs from tissue culture systems.

Dano and Reich (1978, J. Exp. Med. 147: 745–757) have described the production of PAs by cultured C57 black mouse embryo cells that were transformed by infection with murine sarcoma virus. In subsequent studies, Dano et al. (1980, Biochim. Biophys. Acta 613: 542–555) purified PA to homogeneity from cultures of mouse fibroblasts transformed with murine sarcoma virus and showed that its subunits corresponded in electrophoretic mobility in sodium dodecyl sulfate to those of human urokinase.

The recovery of TPA from medium harvested from a human melanoma cell line culture (called the Bowes melanoma cell line) has been reported by Rijken and Collen (1981, Progr. Chem. Fibrinolysis Thrombolysis 5: 236-239). This TPA, which was purified by a variety of chromatographic techniques resulting in a recovery of 1 to 4 mg protein per 10 liters of medium and a 260-fold increase in the specific activity of the purified product as compared to the specific activity in the initial growth medium, was immunologically unrelated to urokinase and absorbed almost completely to fibrin. More recently, Pennica, et al. (1983, Nature 301: 214-221) have cloned the TPA genome from the Bowes melanoma cell line into an E. coli bacterium and have achieved the expression of TPA.

Both a TPA and a UPA have been recovered from supernatants of confluent cultures of a rat prostate adenocarcinoma cell line, PA III (Strickland et al., 1983, Biochemistry 22: 4444-4449). The UPA (45,000 daltons, molecular weight) was purified chromatographically resulting in a recovery of 10 $\mu$g protein per 300 ml medium (at a 66% yield) and a 364-fold increase in specific activity. A second protein (80,000 daltons, molecular weight), believed to be TPA, was not extensively investigated.

Although cultured cells, such as the Bowes melanoma cell line, may produce substantial quantities of TPA, efforts have been made to increase the TPA output of tissue culture systems. In one such effort, Hull et al. (U.S. Pat. No. 3,904,480) developed a method whereby the PA production of cultured kidney cells from a variety of animal species could be increased by maintaining the cell in medium containing low levels of mitotic inhibitors, such as colchicine or vinblastine. No mention was made about whether TPA or UPA was obtained, although since the cells were from kidney, it was probably the latter enzyme. The toxic effects of the sustained exposure to the mitotic inhibitors on the ultimate longevity of the cells was not examined. The degree of enhancement of PA production by their method, compared to production by untreated cells, was also not stated.

In U.S. Pat. No. 4,232,124, Mann describes substantially elevated production of TPA by cultured human diploid fibroblast cells of the MCR-5 strain, in the presence of a TPA inducer. Using lactalbumin hydrolysate as an inducer of TPA synthesis, Mann obtained a dose-dependent response. In the presence of lactalbumin hydrolysate, however, cultures degenerated and precipitated in 6 to 12 days. In contrast, cultures not treated with the inducer could be harvested with repeated medium changes for over a month.

Horiguchi et al. (U.S. Pat. No. 4,328,314) have developed a method for obtaining a 30% to 180% increase in PA production by cultured renal cells of monkey or human origin. This enhanced production of what was most probably UPA was obtained by placing low levels of organic acids, such as fumaric, malic or succinic acid, in the culture medium. Any possible adverse effects on the longevity of treated cells were not described.

From what can be determined based upon the tissue culture references, supra, the harvesting of PA-containing medium from cell cultures (i.e., conditioned medium) can be continued only for a period of about two to perhaps six weeks. After a period of growth which is determined by the characteristics of the cells and the culture medium and conditions, cell degeneration and detachment occurs. When that point is reached, PA production ceases, and the culture vessels must be cleaned, sterilized and reseeded with fresh cells. This relatively limited lifespan of most culture systems is an annoying and costly impediment to efficient TPA production.

3. SUMMARY OF THE INVENTION

The present invention provides a new and significantly improved method for the production of substantial quantities of TPA in a tissue culture system. Through the use of a rat prostate adenocarcinoma cell line cultured under conditions described in the present invention, TPA is obtained which (a) binds strongly to fibrin clots; (b) is neutralized by antibodies directed against TPA; and (c) is resistant to neutralization by antibodies directed against urokinase. As a result, the TPA of this invention is suitable for use in the prophylactic or therapeutic treatment of various cardiovascular conditions and diseases, where uncontrolled blood clotting is a problem. This invention also provides methods for the production of TPA for a period of time which far exceeds that achievable by other cell culture techniques.

According to the method of the present invention, prolonged production of TPA in substantial quantities is attained by alternating the incubation temperature of confluent rat prostate adenocarcinoma cells in vitro as follows: (1) confluent rat prostate adenocarcinoma cells are initially incubated in nutrient medium for a period of about 2 days at a low temperature (e.g., approximately 20° C.-25° C.); (2) subsequently, incubation under standard temperature conditions (e.g., approximately 35° C.-37° C.) is carried out; (3) the culture medium is harvested at the end of the incubation period at the higher temperature. This harvested medium contains high levels of TPA. Fresh nutrient medium may then be added to the confluent rat prostate adenocarcinoma cells which are "recycled" through the low temperature/high temperature incubation protocol described above. Serum-free medium is advantageously used in the entire process and incubations should be carried out in the dark.

The method of the present invention offers a number of advantages over the methods currently used:

(1) the TPA of the present invention is derived from cultures of rat prostate adenocarcinoma cells, thus eliminating the concern over the human melanoma cell origin of other TPAs such as the Bowes TPA;

(2) the rat prostate adenocarcinoma cell line was derived from germ-free rodent stock in which no viral agent has been detected. Similar tumors have been induced in this rat strain by administrations of testosterone; such tumors have not been induced by any infectious or chemical carcinogen.

(3) the rat prostate adenocarcinoma tumor cells are not transplantable, either to other strains of rats or to other mammalian species examined;

(4) the rat prostate adenocarcinoma cells can be cloned, propagated and maintained in serum-free medium and the cells produce TPA when cultured in the serum-free medium, thus, expensive serum is not required for production of TPA;

(5) the rat prostate adenocarcinoma cells produce TPA over periods of months during which high levels of the enzyme are produced every incubation cycle by the same cell culture; in fact, the same flasks of cells have been used for 5 months and the harvested fluids have consistently contained high levels of TPA;

(6) using the culturing method described herein, only TPA, and no detectable levels of urokinase, is produced; therefore, purification of the TPA from the harvested medium by fractionation may not be required;

(7) the TPA is effectively concentrated by placing the harvested cell culture medium in dialysis tubing covered with carboxymethylcellulose (sodium salt);

(8) the TPA produced by the rat prostate adenocarcinoma cell line is not toxic to rats or other mammalian species examined, even when inoculated in very large doses into several strains of rats including the same strain of rat from which the tumor had been derived; and (9) the production of TPA as described herein also offers an advantage over the TPA expressed in genetically engineered bacteria because the steps of cell lysis and the subsequent problems of purification of TPA from a background of host cell proteins are eliminated; moreover, since cotranslational and post-translational modifications of protein structure differ in procaryotes and eucaryotes, the TPA produced by bacterial clones is likely to differ from naturally occurring TPA.

4. DESCRIPTION OF THE INVENTION

According to the method of the present invention, a confluent monolayer culture of a TPA-producing cell line is initially incubated in nutrient medium at a low incubation temperature (e.g., about 20° C. to about 25° C.) for a specified period of time (e.g., about 2 days). The incubation temperature is subsequently increased to a higher temperature (e.g., about 35° C. to about 37° C. which is the typical incubation temperature used in most cell culture techniques) for a period of approximately 24 hours or more. The culture fluids are then harvested and replaced with fresh nutrient medium for repetition of the sequential low/high incubation temperature cycle. The harvested culture medium contains a significant concentration of TPA which can be further concentrated, isolated, and/or purified. The method of the invention can be advantageously practiced using PA III cells (a rat prostate adenocarcinoma cell line), a serum-free nutrient medium, and a 20° C./37° C. incubation temperature cycle carried out in the dark. Interestingly, the PA III cell line produces both urokinase and TPA if cultured at a constant temperature of 37° C. However, when sequentially cycled as described above, TPA is produced at higher concentrations over a remarkably long period of time and urokinase activity is not detectable in the harvested medium.

While the present invention contemplates the use of the PA III cell line, any cell line which produces TPA alone or in conjunction with urokinase and which responds favorably to the culturing conditions set forth above, may be used in the practice of the present invention. Methods for the development of a TPA-producing cell line, propagation of cells in culture, harvesting of cell culture medium and purifying TPA are described in the subsections which follow.

4.1. DEVELOPMENT OF A TPA-PRODUCING CELL LINE

Although many cell types produce plasminogen activator activity, not all produce "tissue-like" plasminogen activator activity (TPA). For example, cultured kidney cells produce only urokinase activity. Other cell types such as fibroblastic, epithelial, or lung cells should thus be used as starting material. Such cells may be of human, porcine, bovine or lapin origin, or from many other species because of the wide distribution of TPA biosynthetic capability. In any event, once a cell type is selected it should be verified that it is TPA either alone or in conjunction with UPA that is produced. Such verification may be made by showing that the activity is neutralized only by antiserum produced against one of the known "tissue-like" TPAs, as described in Section 5.2.4 infra, and that it is adsorbed to insoluble fibrin matrices.

The production of both TPA and UPA by a given cell type may not render use of the cell impractical, as long as substantial levels of TPA are produced. It may be possible, for example, to separate the UPA activity by purification procedures. Alternatively, control of cell culture conditions as described above may be used to enhance TPA synthesis and to suppress UPA production. In the preferred embodiment of this invention, for instance, the cells that are used produce both TPA and UPA when grown at 37° C. When grown under the novel conditions of this invention, however, with an alternating shift in temperature from 20° C. to 37° C., UPA activity cannot be detected although there is strong TPA synthesis (See Section 5, infra).

Once a suitable cell type is selected, the cells may be cultured as fresh explants, maintaining them as normal, diploid cells. Some cells such as human cells will retain the diploid karyotype throughout their lives in culture, although they can be maintained for only a limited number of generations. Then, they undergo senescence and die. Other cells, such as mouse cells, can often be maintained indefinitely in culture. Such cells while initially diploid may undergo a spontaneous transformation to an aneuploid state after a number of generations. Maintenance of these cultures for an indefinite period through subculturing is thus possible. Other cell types may fall between the stably diploid but limited lifespan human cells and the spontaneously transformable, aneuploid and indefinite lifespan mouse cells, in terms of their tendency to spontaneously transform.

Because of their indefinite longevity in cell culture, transformed cells offer advantages for long-term TPA production. Transformed cells may arise spontaneously in vivo, as in the case of strains of mice that invariably develop tumors during the later stages of their lives. Such tumors may be undesirable as TPA producers, however, if they have a tumor virus etiology as do many murine tumors. Spontaneous human tumors, such as the Bowes melanoma, may also be good TPA producers. Where the tumor is of human origin, however, the safety of TPA produced by the cells may be suspect. In the preferred embodiment of this invention, rat spontaneous adenocarcinoma cells are used. Despite rigorous and frequent testing, no viral or other microbiological organism has ever been detected in the cells.

Of course, the aneuploid karyotypic state, and thus indefinite lifespan in culture, could also be actively induced in a desired cell sample. Transformation could be effected by infection with a compatible tumor virus. This procedure should probably be avoided, however, because of the questions of safety already mentioned. Alternatively, transformation could be induced by exposing the cells to ionizing or ultraviolet radiation, or to any one of a number of mutagenic or carcinogenic compounds. Benzo [α] pyrene, N-nitrosodimethylamine, N-nitrosomethylurea, 20-methylcholanthrene and N-methyl-N'-nitro-N-nitrosoguanidine are but a few of the compounds that could be used.

4.2. PRODUCTION OF TPA BY CELLS IN CONFLUENT MONOLAYERS AND COLLECTION OF CULTURE MEDIUM

Tissue selected to produce TPA must generally be broken down into single-cell suspensions. This is most commonly accomplished by mechanical fragmentation with a sterile surgical scalpel, followed by further dispersion by enzymatic and/or chemical treatment. Depending upon the tissue to be dispersed, enzymes such as trypsin, or collagenase may be used, alone or in combination. The action of these enzymes may be further enhanced by divalent metal chelators, such as EDTA or EGTA. Complete dispersal of the tissue cells is not necessary since even sizeable fragments of tissue once in culture may act as growth foci, from which monolayer cell propagation may occur. These resultant monolayers are readily dispersed by enzymatic or chemical means for subsequent subculturing.

The eventual isolation of enzymes such as TPA is facilitated if the macromolecular content of the culture medium is minimized. To accomplish this objective, some cells may be cultured in chemically defined media. Such media may be based upon buffered salt systems such as those of Hanks or Earle, to which essential vitamins, amino acids, fatty acids, glucose and other low molecular weight nutrients have been added. Generally, the absence of some kind of serum must be compensated for by the addition of insulin, corticosteroids, fibroblast growth factor, epidermal growth factor, platelet growth factor, multiplication stimulating activity, or some other serum substitute, but this is not always necessary.

In the preferred embodiment of the present invention, the chemically defined medium of Chan (1981, Prostate 2: 291-298) was first used, but this medium was found to be not as effective as serum-free Dulbecco's modified Eagle's medium. Other standard culture media might also be used without serum such as standard Eagle's medium or media developed by Weymouth or Ham.

Often, cells must be initiated into culture in the presence of 5–10% calf, fetal calf, horse or other serum. Once they are established, however, the cultures may be "weaned" from serum by the gradual reduction of its concentration to the point where it may eventually be eliminated entirely. This "weaning" process may be accomplished quite rapidly in the case of many transformed or tumor cells, since it is well known that these cells often produce growth factors that stimulate their own multiplication and that of other kinds of cells as well.

Once TPA-producing cells are in culture, they must generally attach to a substratum to produce TPA. In the illustrative embodiment of his invention, the simple plastic walls of large culture flasks sufficed. It will be readily understood by those skilled in the art, however, that there are many ways in which the numbers of cells in a culture system may be increased. For example, flasks are available in which the total surface area is increased through a "corrugated" wall design. Similarly, cell attachment surface may be increased through growth on agarose or polyacrylamide microcarrier beads or in perfusion capillary bundles. Production of TPA may also be efficiently scaled up through the use of motorized roller bottle assemblies, which assure efficient exchange at the cell/medium interface.

After the cells have been established in a suitable monolayer culture system, the culture medium may simply be harvested periodically at the end of each low/high temperature cycle and replaced with fresh nutrient medium. The time interval chosen for harvesting should be selected to maximize TPA yields, while at the same time ensuring that the nutritional requirements of the cells are met and that metabolic waste products do not accumulate to the point where medium pH becomes dangerously low.

4.3. PURIFICATION OF TPA FROM THE CULTURE MEDIUM

Any of the innumerable methods known to the protein chemist might be profitably employed to concentrate and purify TPA from the culture medium. Dialysis of the medium against dilute buffer or a superabsorbant material followed by lyophilization might be a good means to remove the bulk of the low molecular weight components of the medium, and to concentrate the TPA. Alternatively, ultrafiltration or precipitation by saturation with salts such as sodium or ammonium sulfate might be used.

Once obtained in concentrated form, any of the standard techniques such as preparative disc gel electrophoresis, ion-exchange chromatography, gel filtration, isoelectric focusing etc. may be used to purify, isolate, and/or to identify the TPA. Those skilled in the art may also readily devise affinity chromatographic means based upon the pronounced adsorption of TPA to insoluble fibrin.

5. EXAMPLE: PA III CELLS

5.1. CONDITIONS FOR THE OPTIMAL PRODUCTION OF TPA BY CULTURED PA III CELLS

Aliquots of a suspension of PA III cells in Dulbecco's modified minimal essential medium (DMEM; GIBCO Laboratories, Grand Island, N.Y.) with 10% heat-inactivated fetal calf serum (heat-inactivated FCS; GIBCO Laboratories, Grand Island, N.Y.) and penicillin (100 units/ml; GIBCO Laboratories, Grand Island, N.Y.)/streptomycin (100 μg/ml; Eli Lilly Co., Indianapolis, IN.) containing $5 \times 10^6$ cells/ml were seeded into 7 liters of the same medium and distributed to 150 cm$^2$ plastic flasks (Corning Glass Works, Corning, N.Y.). The cultures were then incubated at 37° C. until confluent cell monolayers were observed, when the medium was replaced with equivalent volumes of serum-free DMEM containing the same concentrations penicillin/streptomycin. The cultures were then incubated for two days at 20° C. followed by one to two days at 37° C., with light excluded throughout the entire incubation period. The cultures may be incubated in a dry environment or in a humidified environment containing $CO_2$ (e.g., about 2.5% to 5% $CO_2$). After the three to four-day incubation period, the culture fluids were harvested and replaced with an equal volume of fresh serum-free DMEM, and the 20° C./37° C. incubation cycle was repeated.

Because of this unusual incubation schedule, the cultures may be maintained with high level TPA production continuing for at least five months. Throughout this period, no serum or nutrients other than those contained in the DMEM need be added, yet the cells maintain a healthy appearance. In contrast, if the cultures are maintained constantly at 37° C. and the medium is harvested from the cultures at 4-day intervals, the cells degenerate and detach from the surfaces of the flasks within two weeks. Furthermore, the production of TPA under continuous 37° C. incubation is only 50-60% of that observed during the 20° C./37° C. incubation cycle.

5.1.2. ORIGIN AND ESTABLISHMENT OF THE PA III CELL LINE

Ninety-one male germ free (GF) Lobund Wistar rats were maintained under germ free conditions without other experimental intervention for their lifetimes. Lobund Wistar rats were derived from the closed colony of random-bred Wistar rats maintained in Lobund Laboratory, University of Notre Dame. The animals were fed sterile diet, L-485, and water ad libitum (diet L-485 is an all-vegetable diet which was developed in Lobund Laboratory and is manufactured by Tek-Lad Company, Winfield, Iowa). Air, humidity, temperature, light and noise were controlled and maintained at uniform physiological levels. At ages ranging from 22 to 40 months, spontaneous prostate adenocarcinomas developed in 9 of the rats.

Four of these tumors were minced and transplanted subcutaneously into weanling Lobund Wistar rats. The same histologic types of tumors developed in these host animals, along with metastatic lesions predominantly in the lungs, and less frequently, in other organs. One of the transplanted primary tumors, designated PA III, was excised aseptically, washed with sterile phosphate-buffered saline and minced into small fragments. These fragments were then seeded at various dilutions into 8-ounce prescription bottles containing Eagle's minimal essential medium with Earle's salts (MEM; GIBCO Laboratories, Grand Island, N.Y.), 10% heat-inactivated FCS (GIBCO Laboratories, Grand Island, N.Y.), penicillin (100 units/ml, GIBCO Laboratories, Grand Island, N.Y.) and streptomycin (100 μg/ml, Eli Lilly Company, Indianapolis, IN.).

The cultures were incubated at 37° C. until confluent cell sheets were observed. At that point, the medium in each bottle was decanted and replaced with fresh medium, and the cells were detached from the walls of the bottles using a rubber policeman, dispersed by vigorous pipetting, and $5 \times 10^5$ cells were then seeded into new 8-ounce prescription bottles. After cell confluency was again reached, the cells were dispersed with 0.25% trypsin in $Ca^{++}$ and $Mg^{++}$-free Hanks solution, cloned as described by Martin and Tuan (1962, Proc. Soc. Exp. Biol. Med. 123: 138), and propagated by periodic transfer into 150-cm² culture flasks (Corning Glass Works, Corning, N.Y.) in DMEM with 10% FCS and penicillin/streptomycin, as described above.

Stocks of one clone, designated PA III, were grown up through subculturing in DMEM supplemented with 10% heat-inactivated FCS and penicillin/streptomycin. The cells were then stored in culture medium containing 10% glycerol or dimethyl sulfoxide at −70° C., and ampules were rapidly thawed and plated into fresh medium for use as needed. Cells used for TPA production, supra, had been passaged more than 160 times in monolayer culture.

5.2. CHARACTERIZATION OF TPA PRODUCED BY PA III CELLS IN CULTURE

Strickland et al. (1983, Biochemistry 22: 4444-4449) have shown that when the PA III cells are grown at a constant temperature of 37° C., the harvested medium as assayed by chromatographic procedures contains not only an 80,000 dalton molecular weight species believed to be TPA (this species was not extensively investigated by Strickland et al.), but a lower molecular weight "urokinase-like" UPA (45,000 daltons) as well. As a result, the plasminogen activators produced by continuous 37° C. culture of the PA III cells must be fractionated to separate the two.

In contrast, when the PA III cells are cultured according to the method of the present invention (i.e., the low temperature/high temperature incubation cycle described in Section 5.1), the plasminogen activator produced is predominantly the tissue-associated type, TPA.

As described in the subsections below, the identification of TPA in the serum-free culture medium harvested from PA III cells cultured according to the method of the present invention was based upon its molecular weight, fibrin autographs, plasminogen-dependent fibrinolytic effect, thrombolytic effect, fibrin adsorption, and the neutralization of plasminogen activator activity by antiserum directed against TPA and not by antiserum directed against UPA. The typical yield of TPA activity from the harvested PA III serum-free culture medium was 10,000 CTA units per liter of medium. The CTA unit, which is equivalent to the International unit, is the unit established by the Committee on Thrombolytic Agents of the National Heart Institute. It is based on the activity of urokinase, with arginyllysine methyl ester as a substrate (Johnson, A. J., D. L. Kline and N. Alkjaersig. Assay methods and standard preparations for plasmin, plasminogen and urokinase in purified systems. Thromb. Diath. Haemorrh. 21:259, 1969). Furthermore, the TPA produced by PA III cells according to the method of the present invention is stable: it retained its original fibrinolytic effects after storage for 3 months at 4° C., −20° C., and −70° C. Lyophilized preparations after reconstitution were unchanged in their fibrinolytic effects.

5.2.1. MEASUREMENT OF PLASMINOGEN ACTIVATOR THROMBOLYTIC ACTIVITY IN THE PA III CULTURE MEDIUM

That the PA III cell culture harvested medium contained plasminogen activator activity could be readily demonstrated with the following thrombolytic assay: 1.7 ml of the harvested unconcentrated culture medium were mixed with 5 NIH units thrombin (Parke Davis Company, Detroit, MI.; one NIH unit thrombin is that amount of thrombin required to clot 1 ml of standard fibrinogen solution in 15 seconds) and 0.2 mL of fresh rat blood. Rapid clotting occurred, and the mixture was incubated first at 4° C. for 30 minutes, and then for 3 hours in a rotating shaking water bath (50 rotations/minute) at 37° C. Observation at 15-minute intervals revealed that the harvested PA III culture medium fully dispersed the clots within 3 hours of incubation. In contrast, control tubes containing serum-free DMEM showed no thrombolytic effect, even after 18 hours of incubation. The plasminogen activator in the PA III harvested culture medium was also thrombolytic to fibrin clots formed from the blood of mice, guinea pigs, rabbits and human beings as well as preformed clots prepared from rat blood as described below. In contrast to this, the thrombolytic assay system was negative with culture fluids harvested from other cell cultures including rat mammary adenocarcinoma, mastocytoma rat fibroblasts, rat myeloma, mouse L cells and baby hamster kidney cells. Also, substitution of urokinase for the PA III culture fluid (TPA) in the thrombolytic assay system described above resulted in an intact blood clot even after 12 hours.

The TPA produced by PA III cells also dispersed preformed blood clots. In this assay, fresh rat blood (200 µl) was dropped into plastic wells in which it coagulated. TPA from PA III cells (200 µl) was added to the blood clot; control samples received an equal volume of UPA or normal DMEM culture fluids. The wells were incubated at 37° C. and at intervals of 15 minutes the test material was rotated to determine if thrombolysis had occurred. The PA III culture medium dispersed clots within 2.5 hours, but the blood clots of controls containing urokinase or normal DMEM culture fluids remained unchanged after 12 hours.

Thus, the thrombolytic effect by PA III culture fluid was demonstrable in preformed blood clots as well as clots in which the TPA had been incorporated prior to coagulation.

5.2.2. BINDING TO FIBRIN AND FIBRINOLYTIC ACTIVITY

The culture medium harvested from the confluent PA III cells cultured as described in Section 5.1 also produced extensive zones of fibrinolysis on fibrin overlays. This fibrinolytic activity was plasminogen dependent (for method see Pollard et al., 1981, Metastasis of rat prostate adenocarcinoma cells. in: The Prostatic Cell: Structure and Function, Part B; Eds., Murphy, Sandberg and Karr; Alan R. Liss, Inc., N.Y. 249–256). The size of the fibrinolytic plaque produced was dose dependent.

In addition, the culture medium harvested from the confluent PA III cells caused the release of $^{125}I$ from radiolabeled fibrin. The $^{125}I$ release from fibrin was assayed using the procedure described by Reich, E., D. B. Rifkin and E. Shaw, Eds., Protease and Biological Control, Cold Spring Harbor, N.Y. 1975, p. 870. Briefly, plasminogen-free fibrinogen (100 µg/cm² $^{125}I$-fibrinogen) was coated on wells and dried overnight. After washing, the coated wells were incubated with the harvested PA III culture medium for 4–6 hours at 37° in a CO₂ incubator. The supernatant fluid was examined for released $^{125}I$-fibrinopeptides in a gamma counter.

The plasminogen activator activity contained in the culture medium harvested from the PA III cells cultured as described in Section 5.1 adsorbed completely to precipitated fibrin. As reported by Thorson et al. (1972 Thrombosis et Diathesis Haemorrhagica 28: 65–74), such binding is characteristic of TPA; urokinase does not adsorb to precipitated fibrin. Details of the assay used to detect adsorption to fibrin are described below:

0.5 ml of plasminogen-free fibrinogen and 0.4 ml of nutrient fluid harvested from PA III cells cultured according to the method of the present invention were mixed. To this was added 0.1 ml thrombin (2 NIH units/ml) which clots and precipitates fibrin along with PA III fluid trapped within the fibrin clot. After 10 minutes at 37° C., the fibrin clot was disrupted mechanically. Since UPA does not adsorb to fibrin, any UPA that might be present in the trapped PA III culture medium will be released upon disruption of the fibrin clot; TPA, however, will remain adsorbed to the fibrin of the disrupted clot. Therefore, after pelleting the disrupted fibrin clot by centrifugation at 25,000×g for 15 minutes at 4° C., detection of any fibrinolytic activity in the supernatant is an indication of the presence of UPA (not TPA); similarly, the absence of fibrinolytic activity in these supernatants is an indication of the presence of TPA (not UPA). The supernatant fluids thus obtained were assayed on fibrin sheets for evidence of fibrinolytic activity as follows: 20 µl aliquots were placed on fibrin sheets, and after the drops were adsorbed into the fibrin sheet, the fibrin sheet was incubated at 37° C. (in an air tight container to avoid desiccation) for 12 hours. The diameters of any resulting fibrinolytic zones were measured and compared with the zones produced by known concentrations of UPA. No fibrinolytic activity was detected in the supernatants of the medium harvested from the PA III cells cultured and assayed as described above. This complete adsorption of the PA activity to precipitated fibrin indicates the presence of TPA in the harvested PA III culture medium.

5.2.3. MOLECULAR WEIGHT OF THE TPA PRODUCED

The determination of the molecular weight of the PA produced by PA III cells cultured according to the low temperature/high temperature incubation cycle of the present invention was carried out by subjecting concentrated aliquots of the harvested culture medium prepared as described in Section 5.1 to SDS-PAGE (sodium dodecylsulfate polyacrylamide gel electrophoresis) and analyzing the separated polypeptide bands for PA activity by the method of Levin and Loskutoff (1982 J. Cell Biol. 94:631–636). In order to concentrate the TPA, the serum-free media harvested from the PA III cultures were sealed in dialysis bags (porosity 12,000–14,000 daltons molecular weight) which were then covered with carboxymethylcellulose, sodium salt (500,000 daltons molecular weight) for 24 hours at 4° C. As much as an 88 fold concentration of the TPA with a TPA content of 2981 CTA units/mg protein was achieved. After concentration, the contents of the dialysis bags were collected and subjected to SDS-PAGE. Following electrophoresis, the gels were analyzed for PA activity by zymographic analysis as described by Levin and Loskutoff (1982, J. Cell Biol. 94: 631–636). Briefly, the method assays the ability of PA in the SDS gel to lyse fibrin/agar indicator gels. A polypeptide band (80,000 daltons, molecular weight) demonstrated fibrinolytic activity; this polypeptide probably corresponds to TPA. None of the UPA form was detectable using this method; i.e., no polypeptide of 45,000 daltons molecular weight demonstrated fibrinolytic activity.

5.2.4. NEUTRALIZATION OF TPA ACTIVITY BY SPECIFIC ANTISERA

Although the plasminogen activator present in the PA III harvested culture media prepared as described in Section 5.1 had a molecular weight of 80,000 daltons, demonstrated thrombolytic and fibrinolytic activity and bound strongly to fibrin, thus indicating that it was TPA, identification of TPA in the PA III harvested culture medium was further confirmed by immunochemical neutralization tests. These tests compared the TPA derived from culture medium harvested from confluent PA III cells as described in Section 5.1 with urokinase, and with the TPA derived from the Bowes melanoma cell line. The latter material (Bowes cell culture), a generous gift from Dr. Daniel Rifkin, New York University, produced TPA which was purified by the method of Collen et al. (1982, Thromb. Haemostas (Stuttgart) 48: 294-296).

Four different antibody preparations described below were used. (1) anti-TPA/*E. coli:* This antiserum obtained from Dr. Desire Collen had been prepared in goats, using TPA antigen that had been produced by recombinant DNA techniques in *E. coli;* (2) anti-TPA/-Bowes melanoma: This goat IgG prepared against TPA from the Bowes melanoma was obtained from BioPool AB of 591020 Hornefors, Sweden; (3) anti-TPA/porcine heart: BioPool AB also supplied antiserum directed against TPA from porcine heart tissue; and (4) anti-urokinase: Antiserum directed against urokinase was obtained from C. H. Barlow, Michael Reese Medical Center, Chicago, Ill. and from G. Murano, Bureau of Biologics, National Institutes of Health, Bethesda, Md.

Neutralization of plasminogen activator activity by the above specified antisera was determined using a fibrinolytic plaque assay system. The fibrinolysis assay was carried out by the method of Astrup and Mullertz (1982, Arch. Biochem. Biophys. 40: 346-351) as follows.

In the neutralization assay procedure, 10 μl of harvested PA III culture fluid was mixed with 10 μl antiserum (at a 1:10 or 1:5 dilution). After incubation for 15 minutes at 20° C., 20 μl of the mixture was deposited carefully on the surface of precipitated fibrin in petri dishes. The fibrin was then incubated in an air-tight plastic bag for 12 hours at 37° C., and then the diameters of the resulting fibrinolytic plaques were measured. For control purposes, normal serum, or saline was substituted for antiserum. The neutralization effect was quantitated by using constant amounts of harvested PA III medium mixed with known dilutions of antiserum, or by using known dilutions of harvested PA III medium mixed with constant amounts of antiserum. The results are shown in Table I.

TABLE I

NEUTRALIZATION OF PLASMINOGEN ACTIVATOR ACTIVITIES BY SPECIFIC ANTISERA

| Source of PA Activity | Antiserum | Antiserum Dilution or Quantity | Fibrinolytic Plaque Diameter (mm) |
|---|---|---|---|
| PA III TPA[1] | Control | — | 19 |
| | Anti-Urokinase | 1:5 | 19 |
| | | 1:10 | 20 |
| | Control | — | 4.5 |
| | Anti-TPA/*E. coli* | 1:5 | 0 |
| | Control | — | 6.0 |
| | Anti-TPA/Bowes Melanoma | 100 μg | 0 |
| | Anti-TPA/*E. coli* | 1:10 | 0 |
| Bowes TPA | Control | — | 11 |
| | Anti-Urokinase | 1:5 | 11 |
| | Anti-TPA/*E. coli* | 1:5 | 0 |
| | Control | — | 8.0 |
| | Anti-TPA/*E. coli* | 1:5 | 0 |
| Urokinase | Control | — | 8.5 |
| | Anti-urokinase | 1:10 | 0 |
| | Anti-TPA/*E. coli* | 1:10 | 9.0 |

[1]The PA III TPA was obtained from culture medium harvested from confluent PA III cells as described in Section 5.1.

As shown in Table I, PA III TPA activity is neutralized only by antisera that have been prepared against "tissue-like" plasminogen activators, i.e. TPA. Antiserum against urokinase was completely without effect on PA III TPA activity. The TPA activity derived from other sources were also neutralized by TPA antiserum, and these TPAs were also not affected by anti-urokinase antiserum.

5.3. DEPOSIT OF PA III CELL LINE

It is apparent that many modifications and variations of the invention as herein before set forth may be made without departing from the spirit and scope thereof. The specific embodiments are given by way of example only and the invention is limited only by the appended claims.

The PA III cell line described herein was deposited with the American Type Culture Collection (ATCC), Rockville, Md., and has been assigned accession number CRL 8579. It is to be understood that the availability of a deposit does not constitute a license to practice the subject invention in derogation of patent rights granted by the United States government. Furthermore, the present invention is not to be limited in scope by the cell culture deposited, since the deposited embodiment is intended as a single illustration of one aspect of the invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method for the production of tissue plasminogen activator, comprising:
   (a) initially incubating confluent prostate adenocarcinoma cells, having the same characteristics as rat prostate adenocarcinoma cell line PA III deposited with the ATCC and assigned Accession No. CRL 8579, in vitro in nutrient medium at a temperature of about 20° C. to about 25° C. for about 48 hours;
   (b) subsequently incubating the confluent cell culture at a temperature of about 35° C. to about 37° C. for about 24 hours to about 72 hours; and
   (c) harvesting the nutrient medium from the confluent cells.

2. The method according to claim 1 in which the prostate adenocarcinoma cells comprise rat prostate adenocarcinoma cells.

3. The method according to claim 2 in which the rat prostate adenocarcinoma cells comprise PA III cells deposited with the ATCC and assigned Accession No. CRL 8579, or a mutant, recombinant, or genetically engineered equivalent derivative of the CRL 8579 PA III cell line.

4. The method according to claim 1 in which the nutrient medium comprises serum-free medium.

5. The method according to claim 4 in which the serum-free medium comprises serum-free Dulbecco's minimal essential medium.

6. The method according to claim 1 in which the nutrient medium contains an antibiotic.

7. The method according to claim 6 in which the antibiotic comprises penicillin.

8. The method according to claim 6 in which the antibiotic comprises streptomycin.

9. The method according to claim 1 in which incubations are performed in the dark.

10. The method according to claim 1 in which the cells in media are incubated in a dry environment.

11. The method according to claim 1 further comprising;

(d) adding a second aliquot of nutrient medium to the confluent cell culture and repeating steps a, b, and c of claim 1.

12. The method according to claim 1 further comprising concentrating tissue plasminogen activator in the harvested nutrient medium obtained in step c of claim 1.

13. The method according to claim 1 further comprising isolating tissue plasminogen activator from the harvested nutrient medium obtained in step c of claim 1.

14. A method for the production of tissue plasminogen activator, comprising:
  (a) initially incubating confluent rat prostate adenocarcinoma PA III cells in serum-free nutrient medium at a temperature of about 20° C. to about 25° C. for about 48 hours, in the dark;
  (b) subsequently incubating the confluent PA III cell culture at a temperature of about 35° C. to about 37° C. for about 24 hours in the dark; and
  (c) harvesting the serum-free nutrient medium from the confluent PA III cells.

15. The method according to claim 14 further comprising:
  (d) adding a second aliquot of serum-free nutrient medium to the confluent PA III, cells and repeating steps a, b, and c of claim 14.

16. The method according to claim 14 further comprising concentrating tissue plasminogen activator in the harvested serum-free nutrient medium obtained in step c of claim 14.

17. The method according to claim 14 further comprising isolating tissue plasminogen activator from the harvested serum-free nutrient medium obtained in step c of claim 14.

* * * * *